US008568586B2

(12) United States Patent
Cunnien et al.

(10) Patent No.: US 8,568,586 B2
(45) Date of Patent: Oct. 29, 2013

(54) AUTOMATED SYSTEM AND METHOD FOR MONITORING CHROMATOGRAPHY COLUMN PERFORMANCE, AND APPLICATIONS THEREOF

(75) Inventors: Paul Cunnien, Cary, NC (US); Joydeep Ganguly, Boston, MA (US); Basav Ghosh, Apex, NC (US); Asif Ladiwala, San Diego, CA (US); Robert Song, Scituate, MA (US); Jorg Thommes, San Diego, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 379 days.

(21) Appl. No.: 12/863,955

(22) PCT Filed: Jan. 23, 2009

(86) PCT No.: PCT/US2009/000469
§ 371 (c)(1),
(2), (4) Date: Mar. 10, 2011

(87) PCT Pub. No.: WO2009/094203
PCT Pub. Date: Jul. 30, 2009

(65) Prior Publication Data
US 2011/0147312 A1 Jun. 23, 2011

Related U.S. Application Data

(60) Provisional application No. 61/023,747, filed on Jan. 25, 2008.

(51) Int. Cl.
*B01D 15/08* (2006.01)
(52) U.S. Cl.
USPC ......... 210/198.2; 210/85; 210/96.1; 210/101; 210/656
(58) Field of Classification Search
USPC .......... 210/635, 656, 659, 85, 96.1, 101, 143, 210/198.2; 422/70
See application file for complete search history.

(56) References Cited

U.S. PATENT DOCUMENTS 5,039,409 A 8/1991 Blaffert et al.
5,417,853 A 5/1995 Mizuno et al.
(Continued)

OTHER PUBLICATIONS

Hoffmann, M., "Use of ultrasound to monitor the packing of large-scale columns, the monitoring of media compression and the passage of molecules, such as monoclonal antibodies, through the column bed during chromatography," *Journal of Chromatography A* 989:79-94, Elsevier Science B.V., Netherlands (2003).

(Continued)

*Primary Examiner* — Ernest G Therkorn
(74) *Attorney, Agent, or Firm* — Sterne, Kessler, Goldstein & Fox P.L.L.C.

(57) ABSTRACT

The present invention provides automated systems and methods for monitoring column performance in process chromatography, and applications thereof. In an embodiment, column performance is monitored by generating a plurality of process values such as, for example, conductivity values or pH values with a detector during a chromatography step transition between a first mobile phase liquid and a second mobile phase liquid. The process values are transformed to form transformed process values in which noise present in the process values is suppressed. Column performance parameters are calculated based on the transformed process values and displayed during movement of the second mobile phase liquid through the chromatography column. The displayed performance parameters enable an operator to make a determination, for example, regarding the quality of the chromatography column packing and whether to continue the chromatography process or stop the chromatography process until the chromatography column can be repacked or replaced.

17 Claims, 11 Drawing Sheets

(56) References Cited

U.S. PATENT DOCUMENTS

| | | | | |
|---|---|---|---|---|
| 5,641,893 | A | * | 6/1997 | Penn et al. .................. 73/61.53 |
| 5,672,869 | A | | 9/1997 | Windig et al. |
| 5,823,747 | A | | 10/1998 | Ciavarini et al. |
| 6,112,161 | A | | 8/2000 | Dryden et al. |
| 6,311,093 | B1 | | 10/2001 | Brown |
| 6,456,955 | B1 | | 9/2002 | Andrews et al. |
| 2004/0133363 | A1 | | 7/2004 | Vaidyanathan et al. |
| 2005/0285023 | A1 | * | 12/2005 | Liu .............................. 250/221 |
| 2007/0215548 | A1 | | 9/2007 | Zhou |
| 2010/0061605 | A1 | * | 3/2010 | Fain ............................. 382/128 |
| 2011/0147312 | A1 | * | 6/2011 | Cunnien et al. .............. 210/656 |

OTHER PUBLICATIONS

Larson, T.M., et al., "Use of Pross Data To Assess Chromatographic Performance in Production-Scale Protein Purification Columns," *Biotechnol. Prog.* 19:485-492, American Chemical Society and American Institute of Chemical Engineers, United States (2003).

Snyder, L.R., "Column Efficiencies In Liquid Adsorption Chromatography: Past, Present and Future," *Journal of Chromatographic Science* 7:352-360, Preston Publications, United States (1969).

International Search Report and Written Opinion for International Patent Application No. PCT/US2009/00469, International Searching Authority, United States, Mailed on Mar. 25, 2009.

Patent Examination Report No. 1, mailed Nov. 27, 2012 for Australian Patent Application No. 2009206686; 3 pages.

Supplementary European Search Report for European Patent Application No. EP 09 70 4346, mailed on Jun. 18, 2012; 9 pages.

Patent Examination Report, mailed Mar. 9, 2011 for New Zealand Patent Application No. 587161; 2 pages.

* cited by examiner

TABLE 1 – DETECTOR DATA REPRESENTING A CHROMATOGRAPHY STEP-UP TRANSITION

| Volume (L) | Conductivity (mS/cm) |
|---|---|
| 838.921 | 3.91 |
| 839.043 | 3.90 |
| 839.166 | 3.91 |
| 839.288 | 3.92 |
| 839.41 | 3.92 |
| 845.533 | 6.11 |
| 845.656 | 6.78 |
| 845.778 | 7.73 |
| 845.9 | 8.96 |
| 846.023 | 10.55 |
| 846.145 | 12.54 |
| 846.268 | 14.84 |
| 846.39 | 17.88 |
| 846.513 | 21.54 |
| 846.635 | 25.86 |
| 846.758 | 30.87 |
| 846.88 | 36.2 |
| 847.003 | 42.63 |
| 847.125 | 49.97 |
| 847.247 | 57.13 |

| | |
|---|---|
| 848.105 | 114.91 |
| 848.227 | 122.45 |
| 848.349 | 129.11 |
| 848.472 | 135.12 |
| 848.594 | 141.09 |
| 848.717 | 146.4 |
| 848.839 | 151.06 |
| 848.962 | 154.95 |
| 849.084 | 158.27 |
| 849.207 | 161.34 |
| 849.329 | 163.8 |
| 849.452 | 165.75 |
| 849.574 | 167.2 |
| 849.696 | 168.52 |
| 849.819 | 169.56 |

| | |
|---|---|
| 872.595 | 173.97 |
| 872.717 | 173.98 |
| 872.84 | 173.99 |
| 872.962 | 173.98 |
| 873.085 | 174.00 |

FIG.4-1

CHROMATOGRAPHY COLUMN ANALYSIS

LAST ANALYSIS RUN

| | |
|---|---|
| START TIME | 2007-05-15 T 14:11:19 |
| STOP TIME | 2007-05-15 T 14:18:23 |

| | |
|---|---|
| No. of Plates | 143.78 |
| HETP | 0.0953 |
| Skewness | 2.2836 |
| Sigma | 265.7134 |
| Vr | 195.46 |

[START COLLECT]

FIG. 8A

CHROMATOGRAPHY COLUMN ANALYSIS

CURRENT RUN

| | |
|---|---|
| Collection In Progress | START TIME 2007-05-15 T 14:11:19 |
| Analyze In Progress | STOP TIME 2007-05-15 T 14:18:23 |

ADJUSTMENT PARAMETERS

| Column Volume, L | 211.00 |
|---|---|
| Collect Internal, CV | 0.0050 |
| Bed Height, cm | 13.7 |
| Filter Para. 1 | 8 |
| Filter Para 2 | 1 |
| ⋮ | ⋮ |
| Smoothing Para N | 10 |

| | |
|---|---|
| HETP | 0.0953 |
| Skewness | 2.2836 |
| No. of Plates | 143.78 |
| Sigma | 265.7134 |
| Kurtosis | 26.5585 |
| Tau | 7.5176 |
| Vril | 195.46 |
| VRL | 195.46 |
| DC/DV Max | 0.03020 |

FIG. 8B

AUTOMATED SYSTEM AND METHOD FOR MONITORING CHROMATOGRAPHY COLUMN PERFORMANCE, AND APPLICATIONS THEREOF

REFERENCE TO RELATED APPLICATIONS

This application is a 371 of PCT/US09/00469 filed Jan. 23, 2009.

BACKGROUND OF THE PRESENT INVENTION

In the biopharmaceutical industry, process chromatography using packed-bed columns is a key component in the manufacture of complex biological products. In order to ensure product quality and performance (e.g., biological activity), a high packing quality is required. Accordingly, packing quality must be monitored and packed-bed columns having an unacceptable packing quality must be repacked or replaced.

Conventionally, three numeric parameters, namely, the number of plates per column (N), height equivalent to a theoretical plate (HETP), and asymmetry (As), are used to describe the quality of a packed-bed column. These parameters are obtained by performing pulse injections experiments or so-called HETP runs to assess the degree of dispersion of an injected pulse of a non-adsorbed solute.

In accordance with the pulse injection method for assessing packing quality, a well-packed column should have a low HETP value (e.g., less than 0.1 cm). A concept derived from N, HETP provides a measure of broadening in relation to the distance a sample zone has traveled in a chromatography column. A sample zone is the band of a sample in the column, which appears as a peak when it exits the column and is monitored by a detector (analyzer) that corresponds to a certain property of the sample at the column outlet. The mathematical definitions of N and HETP are:

$$N = V_R^2/\sigma^2 \quad (1), \text{ and}$$

$$\text{HETP} = L/N \quad (2),$$

where $V_R$ is a retention volume, which is defined as the volume delivered from the time when half the sample mass is applied to the column to the time when half the sample mass has exited from the column, $\sigma^2$ is the variance of the exit volume distribution, and N is a dimensionless number. L is the column length (or height).

The injected tracer solution in the injected pulse method is assumed to be a Dirac pulse, which has a height of $C_0$ (the initial tracer concentration) and, relative to the column volume, an infinitesimal width. The initial condition corresponds to a column containing only the mobile and stationary phase in equilibrium but without any sample. The injected pulse method also assumes that the distribution of the exit volume of the tracer in the pulse follows, or closely follows, a normal (e.g., Gaussian) distribution curve. Thus, the calculation of N is determined by just three data points from the concentration-volume curve derived during a pulse injection experiment (e.g., the volumes at the peak and at the two points on the curve where the concentration of the tracer is half of the peak concentration). For a normal density function, the width of the curve at half peak height, $W_{1/2}$, is equal to $2\sigma(2\ln 2)^{1/2}$. Therefore, $$\sigma = W_{1/2}/(2(2\ln 2)^{1/2}) \quad (3).$$

Consequently, the calculation of N is given by:

$$N = V_R^2/(W_{1/2}/(2(2\ln 2)^{1/2}))^2 \quad (4),$$

$$N = V_R^2/(W_{1/2}^2/(4(2\ln 2))) \quad (5),$$

$$N = 5.545(V_R/W_{1/2})^2 \quad (6).$$

The value of HETP is obtained by using equation (2) above.

The third parameter, As, used to describe the quality of a packed-bed column, reflects the nature of the peak broadening (e.g. fronting or tailing). As above, in the case of the pulse injection method, just three data points from the entire dataset obtained during a pulse injection experiment are used to determine the value As. This value is calculated by taking the ratio (at 10 percent of the peak height) of the distance between the peak apex and the back side of the chromatographic curve to the distance between the peak apex and the front side of the chromatographic curve. Accordingly, an As value greater than 1 is a tailing peak, while an As value less than 1 is a fronting peak. A well-packed column is assumed to have an As value close to unity.

Because there are frequently situations where the peaks from pulse injection experiments or HETP runs are not Gaussian, the N, HETP, and As values calculated in accordance with the pulse injection method often do not accurately describe the efficiency or packing quality of a column. This is especially true for large process chromatography columns, which routinely give peaks that do not fit a Gaussian distribution. In fact, a calculation that is based on a Gaussian distribution may be insensitive to changes in bed condition or defects in column packing. The reason for this is that if deviations occur somewhere in a transition other than at the few data points used in the calculation, the deviations will not be detected. For the same reason, the pulse injection method is not robust because noise occurring at these critical points will be weighted heavily and lead to incorrect calculations.

In addition to the above noted shortcomings, there are also practical and economical reasons that make the pulse injection method for determining packing quality poorly suited for use in large-scale process chromatography. For example, when running a pulse injection experiment, the volume of the pulse directly affects the results. Since it is difficult to accurately introduce a small pulse into a large column, the reproducibility of HETP runs at the production scale is typically low, especially where subtle changes in the column are concerned. This weakness can render the parameters measured with the pulse injection method unsuitable for use with statistical process control. Furthermore, HETP runs are external to the manufacturing process, and the parameters derived from them are not direct measures of the efficiency or packing quality of the columns when the columns are actually used during the manufacturing process. Column conditions can change between a HETP run and an actual manufacturing process run. When the change is sufficiently large, it can have potentially catastrophic effects on the ensuing process chromatography. Finally, the pulse injection method requires HETP runs to be performed on a regular basis to check the efficiency of the column. These HETP runs consume process resources and can cause delays in production.

What are needed are new monitoring systems and methods that overcome the deficiencies noted above.

BRIEF SUMMARY OF THE PRESENT INVENTION

The present invention provides automated systems and methods for monitoring column performance, and applications thereof. These automated systems and methods are particularly well suited for process chromatography.

In an embodiment, column performance is monitored by generating a plurality of process values such as, for example, conductivity values or pH values with a detector during a chromatography step transition between a first mobile phase liquid and a second mobile phase liquid. The process values are transformed (e.g., by filtering and/or by smoothing) to form transformed process values in which noise present in the process values is suppressed. Column performance parameters are calculated based on the transformed process values and displayed during movement of the second mobile phase liquid through the chromatography column. The displayed performance parameters enable an operator to make a determination, for example, regarding the quality of the chromatography column packing and whether to continue the chromatography process or stop the chromatography process until the chromatography column can be repacked or replaced.

It is a feature of the present invention that it provides a direct measure of chromatography column efficiency and/or packing quality while a monitored column is being used to manufacture product. It is also a feature of the present invention that it can be used to determine chromatography column efficiency and/or packing quality without interrupting or delaying product manufacturing.

Particular embodiments of the present invention include, but are not limited to a first method for monitoring chromatography column performance, comprising: (1) generating a plurality of process values with a detector during a chromatography step transition between a first mobile phase liquid and a second mobile phase liquid; (2) transforming the plurality of process values to form a plurality of transformed process values, wherein the transforming suppresses noise present in the plurality of process values; (3) calculating performance parameters based on the plurality of transformed process values; (4) displaying the performance parameters calculated in (3) during movement of the second mobile phase liquid through the chromatography column; and (5) making a determination, based on the performance parameters displayed in (4), regarding the quality of the chromatography column packing.

In an embodiment, the present invention provides a second method for controlling a chromatography process, comprising: (1) generating a plurality of process values with a detector during a chromatography step transition between a first mobile phase liquid and a second mobile phase liquid; (2) transforming the plurality of process values to form a plurality of transformed process values, wherein the transforming suppresses noise present in the plurality of process values; (3) calculating performance parameters based on the plurality of transformed values during movement of the second mobile phase liquid through a chromatography column; and (4) stopping the chromatography process during movement of the second mobile phase liquid through the chromatography column if a performance parameter calculated in (3) is not within a specified range of values.

In an embodiment of the present invention, step (1) comprises generating a plurality of values selected from the group consisting of (a) conductivity values; (b) pH values; (c) salt concentration values; (d) light absorption values; (e) fluorescence values after excitation with light of a suitable wavelength; (f) refractive index values; (g) electrochemical response values; and (h) mass spectrometry values.

In one embodiment of the present invention, step (2) comprises filtering the plurality of process values. In another embodiment, step (2) comprises smoothing the plurality of process values. In still another embodiment, step (2) comprises calculating a moving average for the plurality of process values.

In an embodiment of the present invention, step (3) comprises calculating one of a plate number (N) value, a height equivalent to a theoretical plate (HETP) value, and an asymmetry (As) value.

In an embodiment, step (5) of the first method comprises making a determination that the quality of the chromatography column packing is unacceptable if a performance parameter calculated in (4) is outside a specified range of values. In one embodiment, an automated alert system is triggered to notify users of the determination.

In an embodiment, step (5) of the first method comprises making a determination that the quality of the chromatography column packing is acceptable if a performance parameter calculated in (4) is inside a specified range of values.

In embodiments, the chromatography column performance is monitored during separation of a biomolecule or pharmacologic compound. In one embodiment, the biomolecule or pharmacologic compound is selected from the group consisting of (a) a protein; (b) a nucleic acid; (c) a carbohydrate; (d) a lipid; (e) a pharmacologically active small molecule; and (f) a hybrid or variant form of any one of (a) through (e).

In embodiments, the chromatography method performed is selected from the group consisting of (a) gas chromatography; (b) liquid chromatography; (c) affinity chromatography; (d) supercritical fluid chromatography; (e) ion exchange chromatography; (f) size-exclusion chromatography; (g) reversed phase chromatography; (h) two-dimensional chromatography; (i) fast protein (FPLC) chromatography; (j) countercurrent chromatography; (k) chiral chromatography; and (l) aqueous normal phase (ANP) chromatography.

In an embodiment of the present invention, a first system for monitoring chromatography column performance is provided. This first system, comprising: a filter that operates on process values corresponding to a chromatography step transition between a first mobile phase liquid and a second mobile phase liquid and outputs filtered process values; a smoothing module that operates on filtered process values received from the filter and outputs transformed process values; a parameter calculator that operates on transformed process values received from the smoothing module and outputs performance parameters indicative of a packing quality of the chromatography column; and a display that displays the performance parameters.

In an embodiment, the first system further comprising: a data collection module that receives process values from a detector and identifies which of the received process values correspond to the chromatography step transition between the first mobile phase liquid and the second mobile phase liquid.

In an embodiment of the first system, the data collection module calculates normalized values for the received process values corresponding to the chromatography step transition between the first mobile phase liquid and the second mobile phase liquid.

In an embodiment of the first system, the smoothing module calculates a moving average for the filtered values.

In an embodiment, the parameter calculator calculates one of a plate number (N) value, a height equivalent to a theoretical plate (HETP) value, and an asymmetry (As) value.

In an embodiment, the display is a computer monitor. The display can include a graphical user interface that enables a user to enter information regarding one of column volume and bed height.

Further embodiments, features, and advantages of the present invention, as well as the structure and operation of various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the present invention and to enable a person skilled in the pertinent art to make and use the present invention.

FIG. 4 is a diagram that illustrates example process data for a chromatography step transition.

Figure 6A:
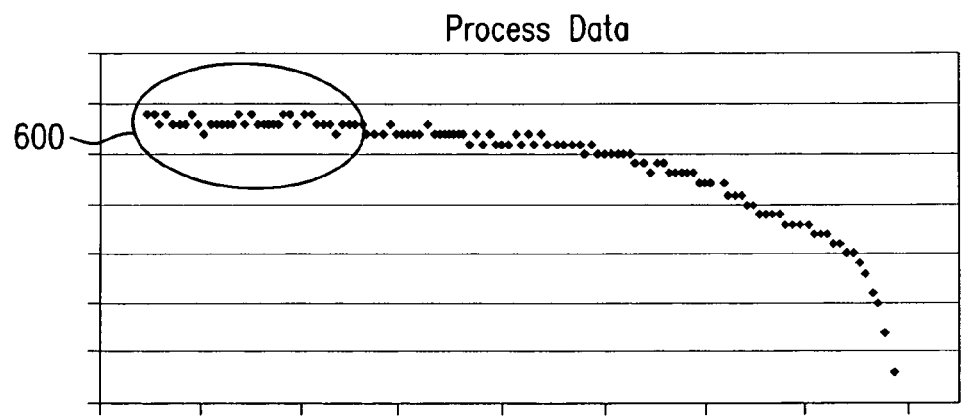
Figure 6B:
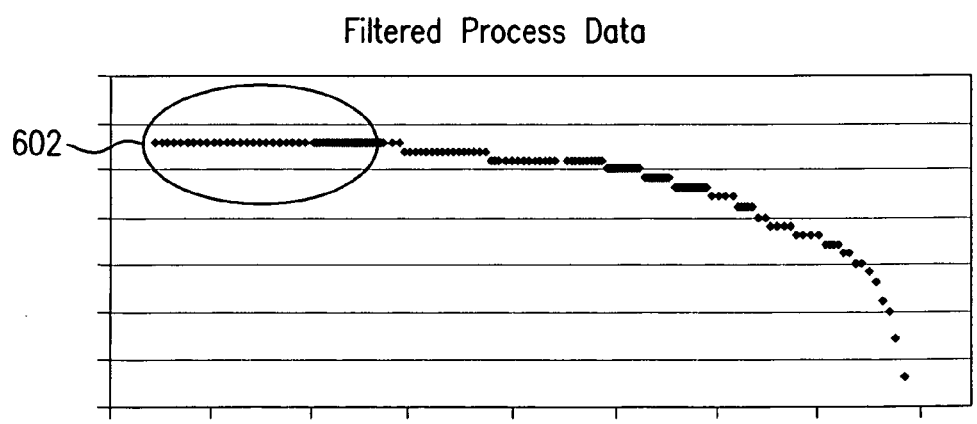

FIGS. 6A-B are graphs that illustrate example effects of a filtering module according to the present invention.

Figure 7A:
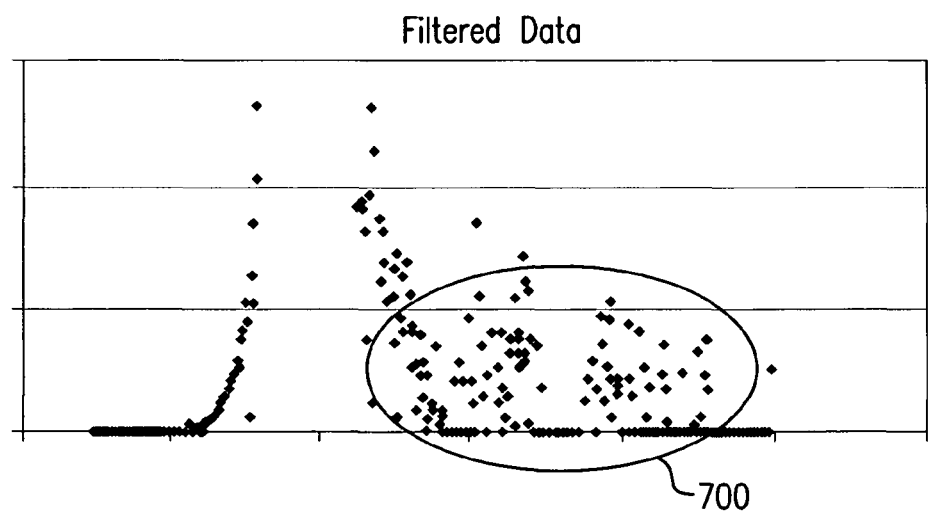
Figure 7B:
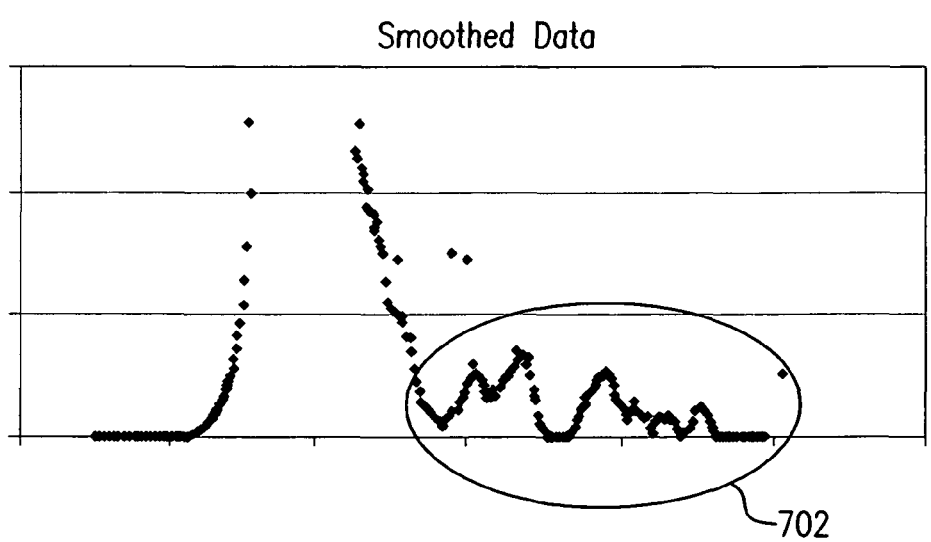

FIGS. 7A-B are graphs that illustrate example effects of a smoothing module according to the present invention.

FIGS. 8A-B are diagrams that illustrate example user interfaces for a process chromatography system according to an embodiment of the present invention.

The present invention is described with reference to the accompanying drawings. The drawing in which an element first appears is typically indicated by the leftmost digit or digits in the corresponding reference number.

DETAILED DESCRIPTION OF THE PRESENT INVENTION

The present invention provides automated systems and methods for monitoring column performance, for example, in process chromatography, and applications thereof. In the detailed description of the present invention that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In an embodiment of the present invention, column performance is monitored by generating a plurality of process values such as, for example, conductivity values or pH values with a detector during a chromatography step transition between a first mobile phase liquid and a second mobile phase liquid. The process values are transformed (e.g., by filtering and/or by smoothing) to form transformed process values in which noise present in the process values is suppressed. Column performance parameters are calculated based on the transformed process values and displayed during movement of the second mobile phase liquid through the chromatography column. The displayed performance parameters enable an operator to make a determination, for example, regarding the quality of the chromatography column packing and whether to continue the chromatography process or stop the chromatography process until the chromatography column can be repacked or replaced.

Figure 1:
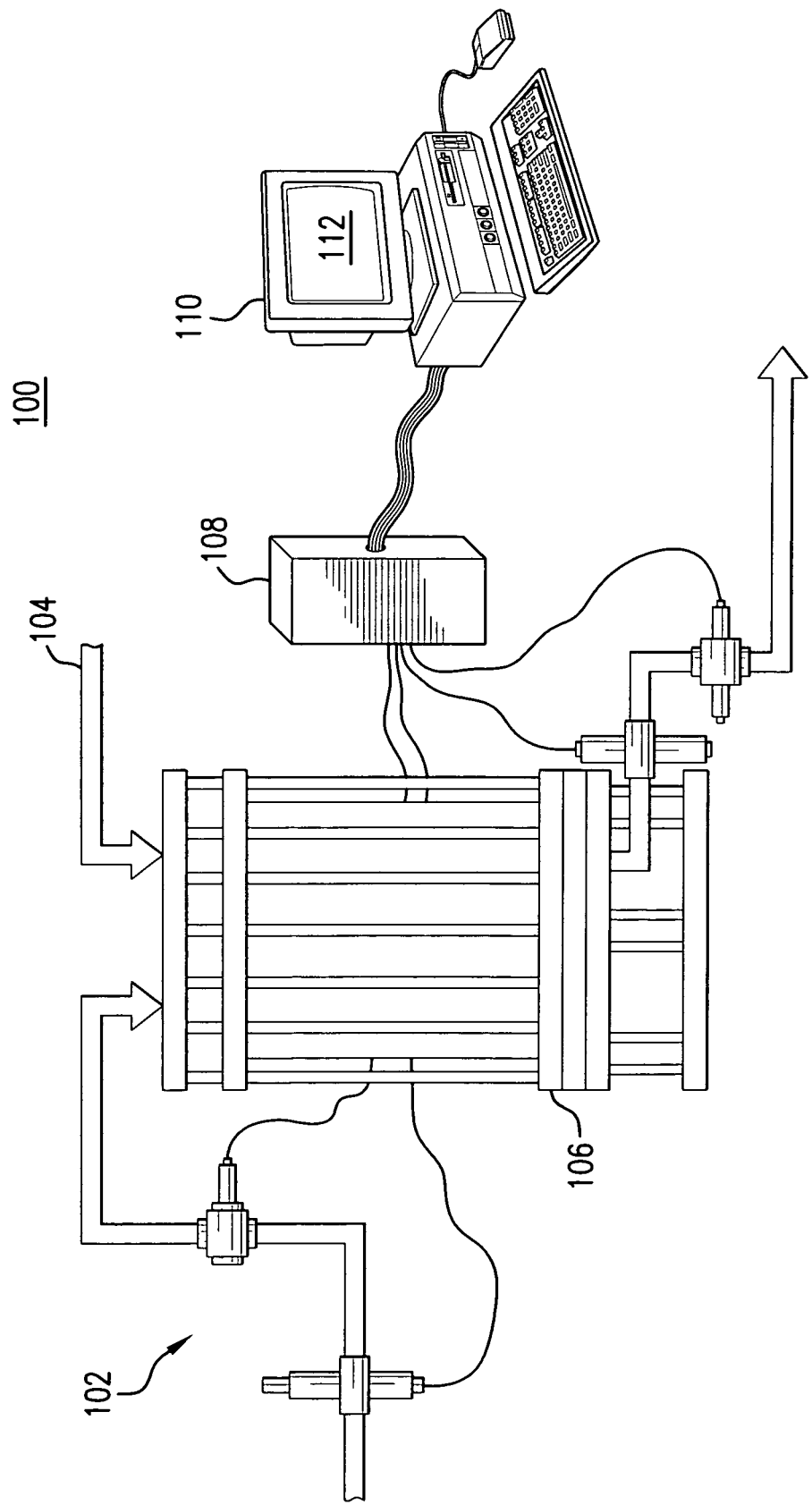
FIG. 1 is a diagram that illustrates an example process chromatography system according to an embodiment of the present invention.

FIG. 1 is a diagram of an example process chromatography system 100 according to an embodiment of the present invention. In embodiments, system 100 is used, for example, to separate biomolecules in a complex mixture, isolate a single biomolecule and/or eliminate contaminants.

As shown in FIG. 1, system 100 includes a mobile phase liquid supply system 102, a material injection system 104, a chromatography or separation column 106, a process controller 108, and an operator's station/computer 110 with a display 112. Mobile phase liquid supply system 102 includes one or more reservoirs that hold and supply the mobile phase liquid(s) used to drive raw materials injected by material injection system 104 through column 106. Pumps belonging to mobile phase liquid supply system 102 impart a high pressure to the mobile phase liquid. In embodiments, the pumps can be used to program the mobile phase liquid(s), for example, by mixing two or more solvents in a particular ratio. Material injection system 104 is used to inject, for example, raw materials requiring separation and/or purification into the mobile phase liquid(s). Chromatography separation column 106 is used to separate and/or purify the injected raw materials.

In an embodiment, process controller 108 and operator's station/computer 110 are used to control process chromatography system 100. Process controller 108 and operator's station/computer 110, for example, react to operator inputs and control operation of the various components of system 100 such as, for example, pumps and valves. In embodiments, one or more elements of system 100, to include portions of process controller 108 and/or operator's station/computer 110, are implemented using a commercially available digital automation system such as the DeltaV™ Digital Automation System available from Emerson Process Management in Austin, Tex.

In an embodiment, as described in more detail below, process controller 108 and operator's station/computer 110 are used to monitor the exit volume or output of column 106 and to make determinations regarding the packing quality or efficiency of column 106. If the packing quality or efficiency of a monitored column is determined to be unacceptable, the operator can stop the chromatography process until the questionable column is repacked or replaced.

Figure 2:
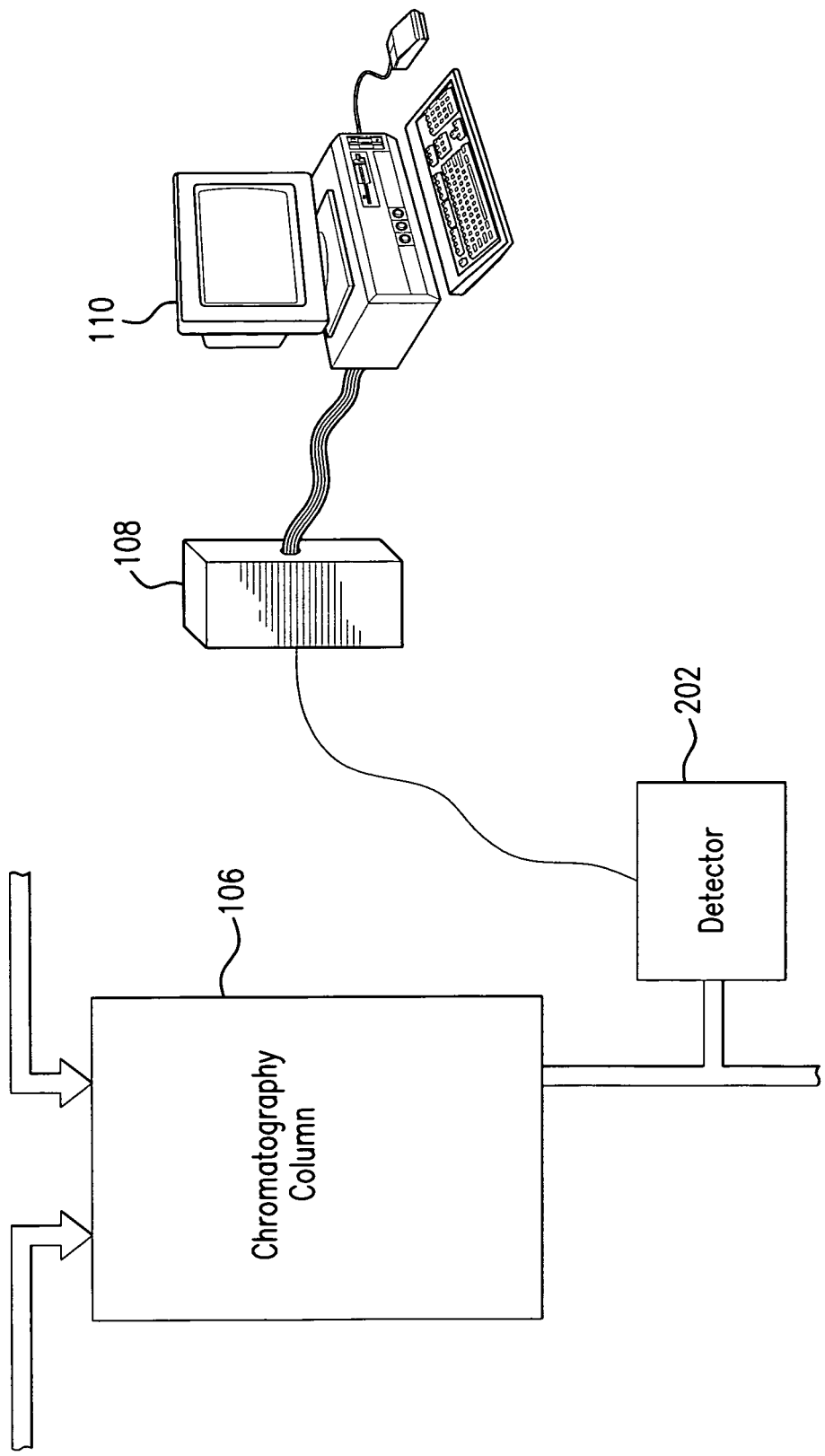
FIG. 2 is a diagram that illustrates a portion of an example process chromatography system according to an embodiment of the present invention.
Figure 5A:
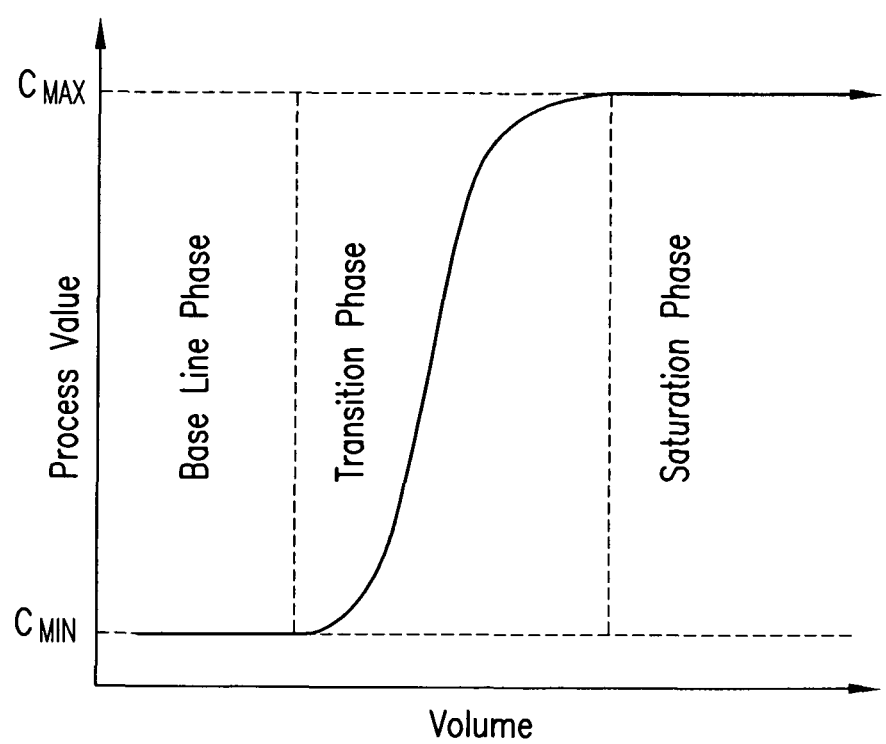
FIG. 5A is a diagram that illustrates an example plot of a chromatography step-up transition.

FIG. 2 is a diagram that illustrates an example detector 202 that is used to monitor the exit volume or output of chromatography column 106 and provide process monitoring data to process controller 108. The process data output by detector 202 is operated upon by process controller 108 and/or operator's station/computer 110 to produce column dispersion parameters or performance parameters. In an embodiment, the process data operated upon to produce the performance parameters is data corresponding to a chromatography step transition between a first mobile phase liquid and a second mobile phase liquid. As used herein, a chromatography step transition is a relatively abrupt change in the mobile phase liquid provided to column 106 that is reflected by a change in a measurable physical characteristic such as, for example, conductivity, pH, etc. A step transition is typically in the form of a breakthrough curve or a washout curve that is due to the replacement of one mobile phase liquid (e.g., solution) by another mobile phase liquid (solution) in a continuously flowing manner. As shown in FIG. 5A, a step transition can be thought of as having three phases (e.g., a baseline phase, a transition phase, and a saturation or plateau phase), and is different than a pulse or a gradient.

In embodiments, detector 202 can be any type of detector that is capable of monitoring process properties useful for determining the efficiency and/or packing quality of column 106. In an embodiment, detector 202 is an electrical conductivity detector. In other embodiments, detector 202 is an ultraviolet (UV) detector, a fluorescence detector, a refractive detector, a pH detector, etc.

Figure 3:
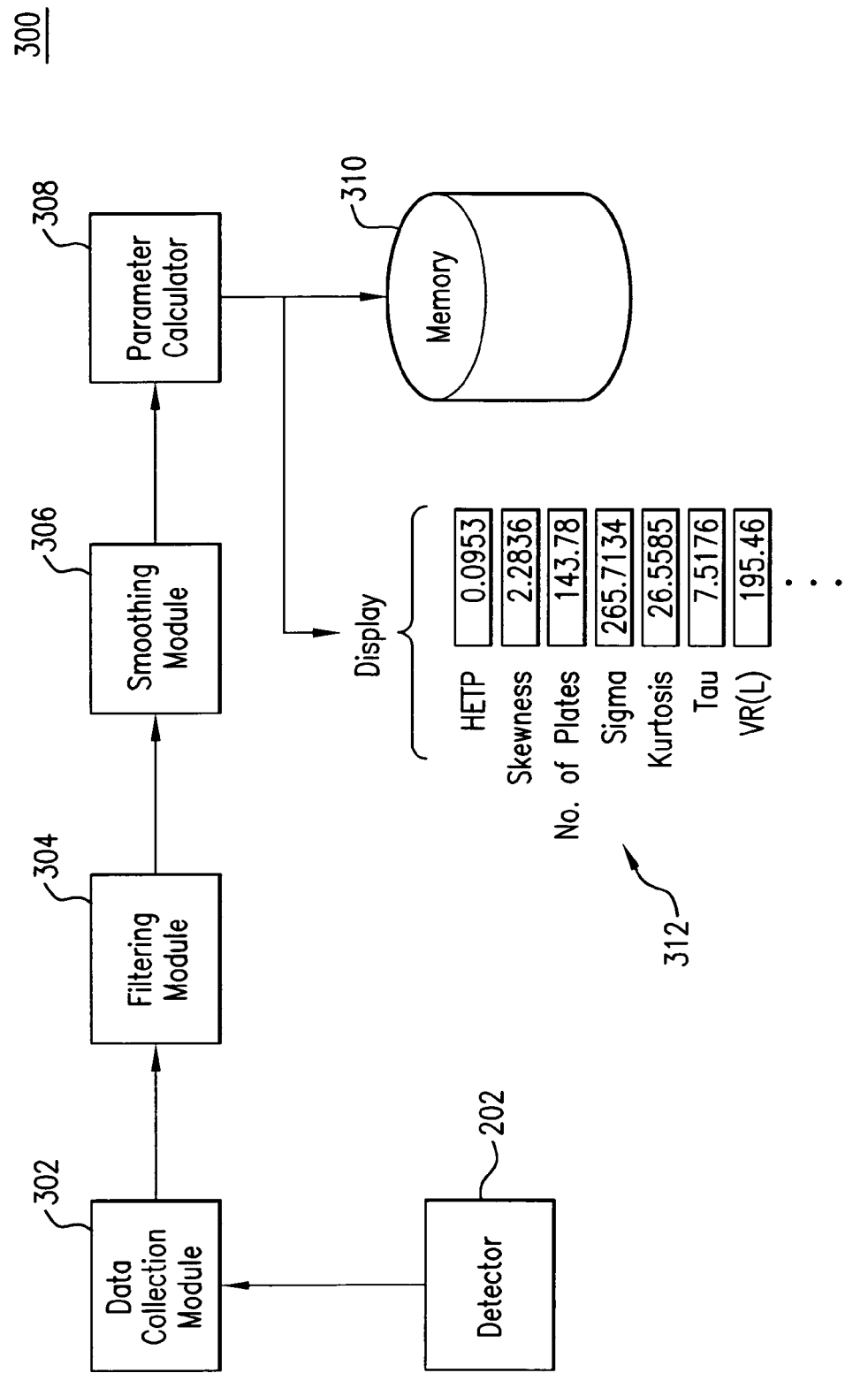
FIG. 3 is a diagram that illustrates an example system for monitoring column performance according to an embodiment of the present invention.

FIG. 3 is a diagram that illustrates an example system 300 for monitoring column performance according to an embodiment of the present invention. As shown in FIG. 3, system 300 includes a data collection module 302, a filtering module 304, a smoothing module 306, a parameter calculator 308 and a memory 310. These modules perform several functions, which include identifying series of process values that correspond to chromatography step transitions, suppressing/filtering out noise present in the process data values, and calculating performance parameters that can be used to monitor column performance.

As noted above, detector 202 is used to monitor liquid exiting chromatography column 106 and output process monitoring data. In an embodiment, the output of detector 202 (e.g., conductivity values) is provided to data collection module 302, which may be a part of controller 108 and/or operator's station/computer 110. Data collection module 302 temporarily stores process data that it receives in a memory.

In embodiments, the exit volume or output of column 106 is sampled on a regular basis and the sample values are sent to data collection module 302. The sampling interval can be either a time-based interval or a volume-based interval. This time-based interval or volume-based interval is user selectable in embodiments using a graphics user interface such as user interface 850 illustrated in FIG. 8B. In one embodiment, the default sample interval is every two seconds, and data collection module 302 has sufficient memory to store a minimum of 180 minutes of sampled data (e.g., data collection module 302 can store at least 5400 sample values). In an embodiment, a volume-based sample rate is used so that the collected data and subsequent processing are not impacted, for example, by starts and stops in the flow of mobile phase liquid or by changes in the flow rate of the mobile phase liquid.

For the purpose of data collection to perform the transition analysis described herein, the t=0 point (i.e., the 0th time point) may be defined as the start of data collection in the phase and/or the point at which the column is brought inline after a pump/system flush. The actual start and end of data collection for transition analysis purposes is an operator-defined transition window having a default range of 0.2 to 2.2 column volumes, with the t=0 being the origin point.

In embodiments of the present invention, the sampling rate used to collect process data values during a chromatography step transition is different (e.g., greater) than for other periods of time so as to minimize the amount of memory needed to store data collected for a particular process chromatography run.

FIG. 4 illustrates example data collected during a chromatography step transition. As shown in FIG. 4, the data includes conductivity values sampled using a volume-based sample interval. In an embodiment, the step transition data that is used for performance parameter calculations, as noted above, is chosen to start at 0.2 column volume instead of at 0.0 column volume. This is to avoid the response signals that are frequently present in the 0.0 to 0.2 column volume area due to a system flush but are not related to the step transition.

In embodiments, the data range is selected to be within 0.2 to 2.2 column volumes because most step transitions are complete within 2 column volumes. The extra 0.2 column volume at the end of the range is to balance the distribution of data around the retention volume ($V_R$) since many step transitions have a tailing. The retention volume is the volume delivered from the time when half the sample mass is applied to the column to the time when half the sample mass has exited from the column. A tailing is a trailing shoulder of a main step transition. Potential causes of a tailing include large void volume in the bed of a column as a result of either uneven distribution of particle (e.g., chromatography medium) sizes or insufficient packing pressure, air under the distribution net (frits), and partial clogging of nets (frits) or chromatography media. In contrast to a tailing, a fronting is a leading shoulder in front of a main step transition. If a fronting is not seen in an original test (e.g., when the column is freshly packed), but appears after reuse and is not alleviated by column cleaning, the cause could be channeling in the bed or development of headspace on top of the bed. Headspace could be either the result of particle redistribution in the column or compacting of the bed. Redistribution of particles happens if the initial distribution of particle sizes in a pack bed is not uniform throughout the column, for example, a column packed under gravity settlement will form a particle size gradient, with large particles settled at the bottom and fine particles on the top. Typically, if a step transition takes more than 2.2 column volumes to complete, the HETP value will be high and investigation is likely warranted.

Filtering module 304 operates on process data received from data collection module 302 and reduces/filters-out noise present in the data. The filtering techniques implemented by filtering module 304 remove noise that might interfere with the accuracy of the performance parameters calculated by parameter calculator 308 while preserving the information contained in the data.

In an embodiment, filtering module 304 reduces or filters out spike noise. Spike noise or spikes are typically present in process data and can be caused, for example, by electrical surges or other types of fluctuations in the electronic measuring equipment of detector 202. These spikes are rises or dips in the detector data that immediately fall back to the values before them. Spikes usually have a relative small magnitude compared to the true response signals. Any available filter or filter technique that reduces/filters-out spike noise can be used.

In an embodiment of the present invention, filtering module 304 implements multiple cascading filters to eliminate/filter-out noise. For example, in an embodiment, a first filter is applied to process data values received from data collection module 302 that operates by comparing the process value before ($C_{i-1}$), and the process value after ($C_{i+1}$), the value being evaluated ($C_i$). If the values $C_{i-1}$ and $C_{i+1}$ are identical, the value $C_i$ is replaced by the value $C_{i+1}$, as shown in Table 1 below. If the values $C_{i-1}$ and $C_{i+1}$ are not identical, the value $C_i$ is unchanged.

TABLE 1

|  | Unfiltered Values | Filtered Value |
|---|---|---|
| $C_{i-1}$ | 3.91 | — |
| $C_i$ | 3.92 | 3.91 |
| $C_{i+1}$ | 3.91 | — |

In the case of high density data sampling, which may occur, for example, during chromatography step transitions, it may be desirable to implement additional filtering as part of filtering module 304. High density data sampling can lead to situations where a spike may interfere with 2-3 process data values in a row. To counter this, additional filtering can be implemented, for example, by comparing a process value $C_{i-2}$ before, and a process value $C_{i+2}$ after, the value $C_i$ being evaluated. If the values $C_{i-2}$ and $C_{i+2}$ are identical, the value $C_i$ is replaced by the value $C_{i+2}$ as shown in Table 2 below. If the values $C_{i-2}$ and $C_{i+2}$ are not identical, the value $C_i$ is unchanged.

TABLE 2

|  | Unfiltered Values | Filtered Value |
|---|---|---|
| $C_{i-2}$ | 3.91 | — |
| $C_{i-1}$ | 3.92 | — |
| $C_i$ | 3.92 | 3.91 |
| $C_{i+1}$ | 3.91 | — |
| $C_{i+2}$ | 3.91 | — |

In embodiments, other filters are also applied to suppress/filter-out spike noise such as the filters illustrated by Table 3 and Table 4 below. For the filter illustrated by Table 3, if the values $C_{i-2}$ and $C_{i+1}$ are equal, the value $C_i$ is replaced by the value $C_{i+1}$. For the filter illustrated by Table 4, if the values $C_{i-1}$ and $C_{i+2}$ are equal, the value $C_i$ is replaced by the value $C_{i+2}$.

TABLE 3

|  | Unfiltered Values | Filtered Value |
|---|---|---|
| $C_{i-2}$ | 3.91 | — |
| $C_{i-1}$ | 3.92 | — |
| $C_i$ | 3.92 | 3.91 |
| $C_{i+1}$ | 3.91 | — |

TABLE 4

|  | Unfiltered Values | Filtered Value |
|---|---|---|
| $C_{i-1}$ | 3.91 | — |
| $C_i$ | 3.92 | 3.91 |
| $C_{i+1}$ | 3.92 | — |
| $C_{i+2}$ | 3.91 | — |

In embodiments, filters may also be implemented as part of filtering module 304, for example, to suppress/filter-out noise that may be present in the leading end or the trailing end of a series of data values associated with a chromatography step transition. Furthermore, the spike noise filters noted herein, as well as other filters, may be applied to the process data values received from data collection module 302 several times, and in an alternating fashion, in order to further suppress/filter-out any spike noise present in the process data values.

Because the influence of noise in calculating column performance parameters is related to the distance of the noise from $V_R$, and the magnitude of the noise is of secondary importance, filtering module 304 implements in embodiments one or more filters that eliminates or suppresses random data spikes by pushing the spikes outwards and away from the transition (e.g., a point one column volume into the step transition). This is accomplished, for example, by comparing the sum of the process data values ($\Sigma\Delta C$) and the sum of the absolute process data values ($\Sigma abs(\Delta C)$) on each side of the transition to identify the presence of noise, and forcing any identified noise outwards away from the mid-point of the transition by replacing a value ($C_i$) that includes noise with the minimum value selected from the values $C_{i-3}$, $C_{i-2}$, $C_{i-1}$, $C_{i+1}$, $C_{i+2}$, and $C_{i+3}$. In embodiments, this filtering operation is used to repeatedly operate on the process values to force the noise outwards from the mid-point of the transition. In one embodiment this filtering operation is repeated, for example, between five and ten times. In embodiments, other filtering operations can be interspersed with these five to ten filtering operations.

In one embodiment, a filtering operation that removes concave and/or convex regions of step transition data is performed ten times after the first occurrence of the above described filter operation. Convex and/or concave regions, if present, are typically found at the beginning and the end of a transition breakthrough curve. The concave/convex removal filter is implemented by adjusting identified convex and/or concave areas using adjacent process values to adjust/flatten the concave/convex region.

In one embodiment, a filter is implemented that eliminates or suppresses random data spikes by pushing the spikes outwards and away from the point of the transition corresponding to the maximum process sample value (e.g., the true mid-point of the step transition rather than the one column volume transition point used above). This filter is implemented similar to the filtering technique described above by comparing the sum of the process data values ($\Sigma\Delta C$) and the sum of the absolute process data values ($\Sigma abs(\Delta C)$) on each side of the maximum process sample value to identify the presence of noise, and forcing any identified noise outwards away from the maximum process sample value by replacing a value ($C_i$) that includes noise with the minimum value selected from the values $C_{i-3}$, $C_{i-2}$, $C_{i-1}$, $C_{i+1}$, $C_{i+2}$, and $C_{i+3}$.

Figure 5B:
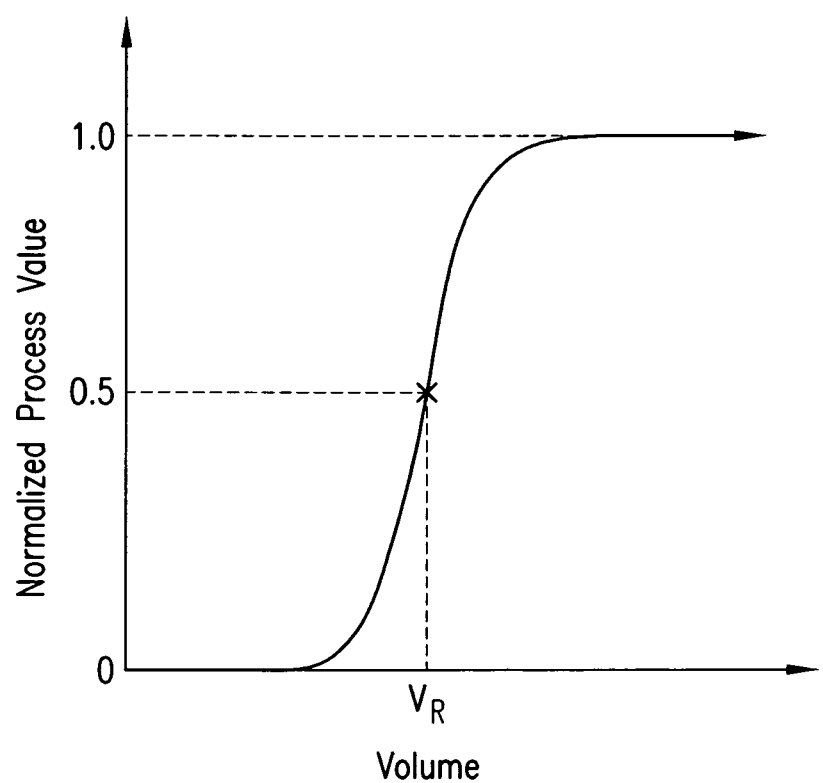
FIG. 5B is a diagram that illustrates an example normalized plot of a chromatography step-up transition.

As noted above, FIG. 5A is a diagram that illustrates an example plot of a chromatography step-up transition. FIG. 5B is a diagram that illustrates an example normalized plot of a chromatography step-up transition. In an embodiment, the last operation performed by filtering module 304 is to normalize the filtered process values. As illustrated in FIG. 5B, normalized values corresponding to a chromatography step transition can be computed using the equation:

$$C_{normalized} = (C - C_{min})/(C_{max} - C_{min}) \tag{7}$$

where $C_{normalized}$ represents a normalized process (e.g., conductivity) value, C represents a data value that is to be normalized, Cmin represents the minimum detector value of the group of values being normalized, and Cmax represents the maximum detector value of the group of values being normalized.

FIGS. 6A-B are graphs that illustrate example effects of a filtering module 304 according to the present invention. Only the first half of the step transition is shown for purposes of clarity.

As illustrated by region 600 of the graph in FIG. 6A, the raw process data output by a detector includes several spikes. As illustrated by region 602 of the graph in FIG. 6B, these spikes are removed when the raw process data is operated upon by filtering module 304. The noise filtering performed by filtering module 304 removes spikes from the process data while leaving the trend information contained in the transition unchanged. Importantly, filtering module 304 eliminates the visible noise/spikes that, if incorporated into the calculations performed by parameter calculator 308, could have large influences on the outcome of the calculations. Filtering module 304 enables the calculations performed by parameter calculator 308 to be accurate and robust.

Smoothing module 306 is used in embodiments to further suppress noise present in the detector data values and to enhance trend information. In one embodiment, smoothing module 306 accomplishes this by applying a moving average algorithm to received data values. The degree of averaging used (e.g., the number of data values averaged together to produce the moving average) in embodiments is determined based on the density of the data. Because the degree of noise reduction is proportional to the square root of the number of data values that are being averaged, noise suppression/reduction is not directly proportional to the number of data values used in the moving average. In embodiments, excessive averaging is avoided in order to ensure that trends in the data are not obscured without an added benefit of increased noise suppression. In embodiments, the number of data values used to implement a moving average are varied depending on the product being processed. Satisfactory results can be achieved using as few as 2-4 data values to produce a moving average. In other embodiments, as many as 10, 20 or 40 points can be used to provide adequate smoothing without apparent flattening of the transition data or degradation of the integrity of the data being smoothed.

In one embodiment, smoothing module 306 takes a moving average of every ten process data points for both volume values and normalized process values to smooth the transition phase of a chromatography step transition. The degree of averaging that allows effective noise suppression is related to the density of the data.

FIGS. 7A-B are graphs that illustrate example effects of a smoothing module 306 according to the present invention. As illustrated by the graph in FIG. 7A, the filtered process data does not always clearly indicate a discernable trend (see, e.g., information in region 700). However, after smoothing by a smoothing module 306 according to the present invention, trend data is clearly shown in region 702 of the graph in FIG. 7B. The effect of smoothing module 702 is to suppress or filter-out hidden noise and enhance trending information contained in the process data.

As noted herein, in embodiments of the present invention, filtering module 304 and smoothing module 306 can be programmed using operator inputs that determine the type of filtering and smoothing operations that are performed and how many iterations of each filtering and smoothing operation are performed. Accordingly, default values are specified for embodiments of the present invention. In one embodiment, these operations and the default values are as follows:

First, the process data received from data collection module 302 is filtered to remove random spikes in the data. For each process value $C_i$, process values $C_{i+b}$ and $C_{i-c}$ are compared. If $C_{i+b}$ equals $C_{i-c}$, the value $C_{i+c}$ is used to replace the value $C_i$. Otherwise, the value $C_i$ is not altered. This filtering process is repeated (i.e., iterated) in accordance with the width of an operator specified array [(b, c)]. If no input array is specified, the default array is Default: [(b, c)]=[(1, 1), (2, 2), (1, 1), (2, 1), (1, 1), (1, 2), (1, 1), (1, 1)].

Next, the process data is filtered for noise by computing a sum of the process values ($\Sigma \Delta C$) and a sum of the absolute process values ($\Sigma abs(\Delta C)$) on either side of the volume equal to one column volume (e.g., a left hand side of the transition (L: 0<V<1 Column Volume) and a right hand side of the transition (R: V/1 Column Volume). For process value $C_i$ on the left hand side, if $\Sigma \Delta C_{L,i} = \Sigma abs(\Delta C)_{L,i}$, the value $C_i$, is not altered. Otherwise, $C_i$ is replaced with the minimum value of $(C_{i-n}:C_{i+n})$, where n is a user-defined parameter. For process value $C_i$ on the right hand side, if $\Sigma \Delta C_{R,i} = \Sigma abs(\Delta C)_{R,i}$, the value $C_i$, is not altered. Otherwise, $C_i$ is replaced with the maximum value of $(C_{i-n}:C_{i+n})$. This filtering operation is repeated "r" times for different values of n, where r is an operator-defined parameter. If no values are specified, the default values are Default: n=3; r=1=width of array [n]

Concave and/or convex regions of the transition process data are removed by computing values on the left side and the right side of the one column volume value. These concaves or convexes are typically caused by brief pauses in mobile phase liquid flow. For the value $C_i$ on the left hand side, the value $C_i$ is set to $C_{i+1}$ if $\Delta C_{i+1} < 0$ and $C_i > C_{min}$. Otherwise, $C_i$ is not altered. For the value $C_i$ on the right hand side, Ci is set to $C_{i-1}$ if $\Delta C_i < 0$ and $C_i < C_{max}$. Otherwise, $C_i$ is not altered. Finally, the new right hand side and left hand side values are combined to get the new values for C. This filtering process is iterated "m" times to smooth out convex/concave regions in the transition data, where m is an operator-defined parameter. The default value is Default: m=10.

The next noise filter to be applied is similar to that described above. First, the values $\Sigma \Delta C$ and $\Sigma abs(\Delta C)$ are calculated on either side (i.e., left hand (L) and right hand (R)) of the one column volume value. For $C_i$ on the left hand side, if $\Sigma \Delta C_{L,i} = \Sigma abs(\Delta C)_{L,i}$, $C_i$, is not altered. Otherwise, $C_i$ is set to the minimum of $(C_{i-n}:C_{i+n})$. For $C_i$ on the right hand side, if $\Sigma \Delta C_{R,i} = \Sigma abs(\Delta C)_{R,i}$, $C_i$ is not altered. Otherwise, $C_i$ is set to the maximum of $(C_{i-n}:C_{i+n})$. The filtering is repeated "p" times for different values of n, where p and n are operator-defined parameters. The default is Default: n=4, 5, 10, 20, 30, 30; p=6=width of array [n].

The next filtering technique applied is to compute $\Sigma \Delta C$ and $\Sigma abs(\Delta C)$ on either side of $V\_\Delta C_{max}$ (i.e., the volume value corresponding to $\Delta C_{max}$). For the value $C_i$ on the left hand side, if $\Sigma \Delta C_{L,i} = \Sigma abs(\Delta C)_{L,i}$, the value $C_i$, is not altered. Otherwise, $C_i$ is set to $C_{min}$. For the value $C_i$ on the right hand side, if $\Sigma \Delta C_{R,i} = \Sigma abs(\Delta C)_{R,i}$, $C_i$ is not altered. Otherwise, $C_i$ is set to $C_{max}$. The filtering process is repeated "q" times, where q is an operator-defined parameter. The default is Default: q=1.

After filtering by filtering module 304, the filtered process values are normalized in the manner described above.

After normalization, the normalized, filtered process values are smoothed by taking a moving average of the filtered process values and the volume value to generate smoothed process values and smoothed volume values. This is done using an N point moving average algorithm where N is an operator-defined value. The default value for N is Default: N=10.

In an embodiment, system 300 is capable of providing visual representation (i.e., plots) for the following on display 112 of $C_{normalized}$ (post-filtering) vs. V; $\Delta C$ (post-filtering) vs. V; and $\Delta C$ (post-filtering and moving average smoothing) vs. V. The operator has the option and flexibility to turn-on and turn-off this plotting feature.

Parameter calculator 308 operates on the data values received, for example, from smoothing module 306 and generates one or more performance parameters 312 that can be used to evaluate the packing quality and/or efficiency of chromatography column 106. In an embodiment, parameter calculator 308 calculates one or more of the performance parameters 312 (e.g., HETP, Skewness, N, Sigma, Kurtosis, Tau, $V_R$, etc.) illustrated in FIG. 3. Performance parameters 312 are displayed in embodiments on a user interface display so that an operator overseeing operation of chromatography system 100 can monitor the performance parameters and determine whether one or more performance parameter values exceed or are outside of an acceptable range of values, thereby indicating that chromatography column 106 may need to be repacked or replaced. In an embodiment, when an operator identifies, for example, that a performance parameter 312 exceeds or is outside of an expected operating range of values, the operator checks the column or can contact a more experienced individual such as, for example, a supervisor to determine whether it is acceptable to continue the chromatography process or whether the process should be discontinued until the column can be repacked or replaced.

For purposes of calculating performance parameters 312, process chromatography step transitions are treated as cumulative frequency distribution curves of exit volume. Statistical parameters of the exit volume distribution, and the subsequently derived dispersion parameters, are directly calculated from the step transition data, after being filtered and/or smoothed as described herein. No assumption is made that the distribution of exit volume follows any predetermined function. Thus, the present invention can be adequately applied to step transitions of different shapes. Furthermore, the Skewness parameter, which is determined by taking into account the entire dataset from a step transition without making any assumptions about the distribution of the curve, is used to describe the asymmetry of the column. This is markedly different from conventional asymmetry calculations, which only uses the data points from a dataset.

In an embodiment, the values $\Delta C$ and $\Delta C/\Delta V$ are computed based on the normalized process values ($C_{normalized}$) and the volume values (V) described above. Calculations for N, HETP, Skewness, Kurtosis, $\sigma^2$, $V_R$ and $V_R 1$, $\Delta C/\Delta V\_max$ and $\tau$ (min) are performed using the integral equations provided below, where C in the equations refers to the normalized process values ($C_{normalized}$) described above.

$$V_R 1 = V_{\Delta C_{max}} + \int_0^1 (V - V_{\Delta C_{max}}) dC \tag{8}$$

$$V_R = \int_0^1 V dC = V_R 1 + \int_0^1 (V - V_R 1) dC \tag{9}$$

$$\sigma^2 = \int_0^1 (V - V_R) dC \tag{10}$$

$$\text{Skewness} = \left[ \int_0^1 (V - V_R)^3 dC \right] \Big/ (\sigma^2)^{3/2} \tag{11}$$

$$\text{Kurtosis} = \left[ \int_0^1 (V - V_R)^4 dC \right] \Big/ (\sigma^2)^2 \tag{12}$$

Memory 310 is used to store performance parameters 312 as well as other values that are useful for evaluating operation of chromatography system 100. In embodiments, memory 310 can be any type of available memory such as, for example, a computer hard drive memory, flash memory, optical drive memory, tape memory, etc. In an embodiment, memory 310 stores the transition analysis data and the calculated results in an output file. This data can be used, for example, to plot trends in the calculated transition analysis parameters (e.g., N, HETP, Skewness, Kurtosis, $\sigma^2$, $V_R$, etc.) across a set of process cycles and/or batches. The operator has the option in embodiments to turn-on and turn-off this plotting feature. In embodiments, calculated performance parameters are stored in a continuous historian and a batch historian data structure.

As will be understood given the description herein, system 300 can be used to cover both ends of each chromatography by analyzing a step before a product/sample is loaded onto a column and another step after the product/sample is eluted from the column. Monitoring the step before loading enables an operator to determine whether the column packing quality is sufficient for the ensuing steps to continue. The monitoring step afterwards indicates, for example, whether the packing quality was retained throughout a purification process.

FIGS. 8A-B are diagrams that illustrate example user interfaces for a process chromatography system according to an embodiment of the present invention. In embodiments, the user interfaces display performance parameters and other information that enable a chromatography process operator to effectively and efficiently manage operation of a chromatography system. In particular, the performance parameters that are displayed permit an operator to evaluate the quality of a chromatography column packing and determine whether the column is performing as expected.

FIG. 8A is a diagram of an example graphical user interface 800. As shown in FIG. 8A, user interface 800 includes date-time displays 802, performance parameter displays 804, a data collection start button 806, and shortcut icons 808. The date-time displays 802 include a display that identifies the start date and time and the stop date and time of the last chromatography transition analysis run. Performance parameter displays 804 display several performance parameters such as, for example, values for N, HETP, skewness, etc. As described herein, the displayed performance parameters provide process chromatography operators a reliable, visual inspection of column performance, and they can be used to determine when process adjustments are needed. The displayed performance parameters also enable an operator to determination whether the chromatography column should be repacked or replaced. The data collection start ("Start Collection") button is used to initiate the collection of process data. The shortcut icons 808 are used to launch other applications and/or features of the present invention described herein such as, for example, graphing and control features.

FIG. 8B is a diagram of an example graphical user interface 850. As shown in FIG. 8B, user interface 850 includes date-time displays 802, performance parameter displays 852, current transition analysis status displays 854, and program adjustment parameters 856. The date-time displays 802 display information regarding the date and time of the last transition analysis run. Performance parameter displays 852 display most or all of the performance parameters described herein and includes several parameters not shown on user interface 800. Current transition analysis status displays 854 display the progress/status of a current transition analysis run. Program adjustment parameters 856 are used for inputting and editing program parameters that control, for example, operation of filtering module 304 and smoothing module 306 of system 300.

In embodiments of the present invention, user interfaces 800 and 850 can be modified to include additional features. For example, in embodiments, when one of the displayed performance parameters is outside of its normal operating range, the color of the display is changed, thereby drawing the operator's attention to the change.

As will become apparent to persons skilled in the relevant art given the description herein, it is a feature of the present invention that, in addition to being able to be used to recognize conditions that require a column to be repacked such as, for example, channel formation, a dried column, air bubble accumulation under the flow distributor, etc., the invention can equally well be used to confirm that a column does not require repacking. In many instances, companies repack columns needlessly due to a lack of objective evidence regarding the quality of the columns. By using the present invention to confirm the quality of a column's packing, companies can avoid the labor and material costs associated with repacking columns that maintain their packing quality after multiple reuses. In addition, the present invention can be used to evaluate different packing procedures (e.g. gravity settlement versus continuous flow of slurry).

Other features of the present invention described herein include an ability to directly calculate column dispersion parameters from a step transition without converting the transition data into a peak, new techniques for reducing noise present in process data, and using skewness to describe the asymmetry of a transition. These features of the present invention, as well as other features, enable one to calculate values of N, HETP, and skewness accurately from step transition datasets. These calculated values or performance parameters are both sensitive to subtle changes that can develop in a column over time, and they are capable of detecting gross integrity breaches in a column. The performance parameters calculated in accordance with the present invention can also be used, for example, to improve the statistical process control (SPC) of production chromatography.

The systems and methods of the present invention are useful for application to a wide-variety of chromatographic methods. For example, some types of chromatographic methods that may be used include, but are not limited to: gas; liquid (for example, but not limited to, high performance liquid chromatography (HPLC)); affinity (for example, but not limited to, antibody affinity, Fc-receptor affinity, and ligand-receptor affinity chromatography); supercritical fluid; ion exchange; size-exclusion; reversed phase; two-dimensional; fast protein (FPLC); countercurrent; chiral; and, aqueous normal phase (ANP) chromatography.

The present invention is also particularly useful, for example, in the production and manufacturing of biologics and pharmaceutical (or pharmacological) compounds. For example, a small sampling of the variety of different types of biologics and pharmaceutical compounds that can be produced using methods and systems of the present invention are shown below. The general categories and specific examples of molecules and compounds listed here are for purposes of exemplification only (to provide a sampling of examples) and are not to be construed as limiting to the present invention. Examples of Biomolecules; Small and Large ("Macro") Molecules Proteins/polypeptides/peptides (for example, but not limited to, recombinant proteins, recombinant fusion proteins, antibodies/immunoglobulins, glycoproteins, peptide hormones, complement proteins, coagulation factor proteins, enzymatic proteins, receptor proteins, protein ligands, structural proteins, metalloproteins);

Nucleic acids/polynucleotides (for example, but not limited to, deoxyribonucleic acid (DNA) and ribonucleic acid (RNA) molecules including, for example, but not limited to, single-, double-, triple-, and quadruple-stranded forms thereof, as well as for example, but not limited to, A-, B- and Z-DNA forms of nucleic acid molecules);

Carbohydrates/polysaccharides (for example, but not limited to, monosaccharides, disaccharides, oligosaccharides, polysaccharides);

Lipids (including, for example, but not limited to, fats, oils, waxes, cholesterol, sterols, fat-soluble vitamins (such as vitamins A, D, E, K), monoglycerides, diglycerides, phospholipids, fatty acid esters, fatty acyls, glycerolipids, glycerophospholipids, sphingolipids, sterol lipids, prenol lipids, saccharolipids, polyketides);

Other small molecules, organic compounds, and pharmacologically active molecules (for example, but not limited to, amino acids, steroid hormones, amine-derived hormones); and, Hybrids and variants of any of the above (for example, covalently-linked nucleic acid/polypeptide hybrids as wells as any other combination or variation of the above compounds such as, for example, labeled or "tagged" compounds (such as radiolabeled compounds or compounds coupled with toxic or other therapeutic components (e.g., pegylated compounds))).

The foregoing description of the specific embodiments will so fully reveal the general nature of the invention that others can, by applying knowledge within the skill of the art, readily modify and/or adapt for various applications such specific embodiments, without undue experimentation, and without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

It is to be noted that while many of the examples features described herein have made references to chromatography step-up transitions, the present invention works equally well for both step-up and step-down transition. Furthermore, the present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The breadth and scope of the present invention should not be limited by any of the above-described exemplary embodiments, but should be defined only in accordance with the following claims and their equivalents. In addition, it is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A system for monitoring chromatography column performance, comprising:
    a filter that operates on process values corresponding to a chromatography step transition between a first mobile phase liquid and a second mobile phase liquid and outputs filtered process values, wherein the filter is configured to reduce or filter out spike noise;
    a smoothing module that operates on filtered process values received from the filter and outputs transformed process values;
    a parameter calculator that operates on transformed process values received from the smoothing module and outputs performance parameters indicative of a packing quality of the chromatography column; and
    a display that displays the performance parameters.

2. The system of claim 1, further comprising:
    a data collection module that receives process values from a detector and identifies which of the received process values correspond to the chromatography step transition between the first mobile phase liquid and the second mobile phase liquid.

3. The system of claim 2, wherein the data collection module calculates normalized values for the received process values corresponding to the chromatography step transition between the first mobile phase liquid and the second mobile phase liquid.

4. The system of claim 1, wherein the filter operates on conductivity values.

5. The system of claim 1, wherein the smoothing module calculates a moving average for the filtered values.

6. The system of claim 1, wherein the parameter calculator calculates one of a plate number (N) value, a height equivalent to a theoretical plate (HETP) value, and an asymmetry (As) value.

7. The system of claim 1, wherein the display is a computer monitor.

8. The system of claim 1, wherein the display includes a graphical user interface that enables a user to enter information regarding one of column volume and bed height.

9. The system of claim 1, wherein the chromatography column performance is monitored during separation of a biomolecule or pharmacologic compound.

10. The system of claim 9, wherein said biomolecule or pharmacologic compound is selected from the group consisting of:
   a) a protein;
   b) a nucleic acid;
   c) a carbohydrate;
   d) a lipid;
   e) a pharmacologically active small molecule; and
   f) a hybrid or variant form of any one of a) through e).

11. The system of claim 1, wherein the chromatography performed is selected from the group consisting of:
   a) gas chromatography;
   b) liquid chromatography;
   c) affinity chromatography;
   d) supercritical fluid chromatography;
   e) ion exchange chromatography;
   f) size-exclusion chromatography;
   g) reversed phase chromatography;
   h) two-dimensional chromatography;
   i) fast protein (FPLC) chromatography;
   j) countercurrent chromatography;
   k) chiral chromatography; and
   l) aqueous normal phase (ANP) chromatography.

12. The system of claim 1, wherein the filter is configured to:
   (a) compare a process value ($C_i$) with a corresponding process value before ($C_{i-1}$), and a corresponding process value after ($C_{i+1}$), and
   (b) replace $C_i$ with $C_{i+1}$ if $C_{i+1}$ and $C_{i-1}$ are identical or maintain $C_i$ if $C_{i+1}$ and $C_{i-1}$ are not identical.

13. The system of claim 1, wherein the filter is configured to:
   (a) compare a process value ($C_i$) with a corresponding process value before ($C_{i-2}$), and a corresponding process value after ($C_{i+2}$), and
   (b) replace $C_i$ with $C_{i+2}$ if $C_{i+2}$ and $C_{i-2}$ are identical or maintain $C_i$ if $C_{i+2}$ and $C_{i-2}$ are not identical.

14. The system of claim 1, wherein the filter is configured to:
   (a) compare a process value ($C_i$) with a corresponding process value before ($C_{i-2}$), and a corresponding process value after ($C_{i+1}$), and
   (b) replace $C_i$ with $C_{i+1}$ if $C_{i-2}$ and $C_{i+1}$ are identical or maintain $C_i$ if $C_{i+1}$ and $C_{i-2}$ are not identical.

15. The system of claim 1, wherein the filter is configured to:
   (a) compare a process value ($C_i$) with a corresponding process value before ($C_{i-1}$), and a corresponding process value after ($C_{i+2}$), and
   (b) replace $C_i$ with $C_{i+2}$ if $C_{i-1}$ and $C_{i+2}$ are identical or maintain $C_i$ if $C_{i+2}$ and $C_{i-1}$ are not identical.

16. The system of claim 1, wherein the filter includes one or more filters that are applied to the process values several times and in an alternating fashion.

17. The system of claim 1, wherein the filter is configured to:
   (a) compare the sum of the process data values ($\Sigma\Delta C$) and the sum of the absolute process data values ($\Sigma abs(\Delta C)$) on each side of the maximum process sample value to identify the presence of noise, and
   (b) replace a process value ($C_i$) that includes noise with the minimum corresponding process value selected from the group consisting of $C_{i-3}$, $C_{i-2}$, $C_{i-1}$, $C_{i+1}$, $C_{i+2}$ and $C_{i+3}$.

* * * * *